United States Patent
McGee

(10) Patent No.: US 8,801,617 B2
(45) Date of Patent: Aug. 12, 2014

(54) FAR-FIELD AND NEAR-FIELD ULTRASOUND IMAGING DEVICE

(75) Inventor: David McGee, Sunnyvale, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 13/400,253

(22) Filed: Feb. 20, 2012

(65) Prior Publication Data

US 2012/0245469 A1 Sep. 27, 2012

Related U.S. Application Data

(60) Provisional application No. 61/466,107, filed on Mar. 22, 2011.

(51) Int. Cl.
*A61B 8/00* (2006.01)

(52) U.S. Cl.
USPC ........... 600/462; 600/437; 600/459; 600/466; 600/467

(58) Field of Classification Search
USPC .................................. 600/437, 439, 459, 462
See application file for complete search history.

(56) References Cited

U.S. PATENT DOCUMENTS

| | | |
|---|---|---|
| 5,372,138 A | 12/1994 | Crowley et al. |
| 5,377,685 A | 1/1995 | Kazi et al. |
| 5,379,772 A | 1/1995 | Imran |
| 5,383,874 A | 1/1995 | Jackson et al. |
| 5,445,155 A | 8/1995 | Sieben |
| 5,485,849 A | 1/1996 | Panescu et al. |
| 5,494,042 A | 2/1996 | Panescu et al. |
| 5,588,432 A | 12/1996 | Crowley |
| 5,606,975 A | 3/1997 | Liang et al. |
| 5,833,621 A | 11/1998 | Panescu et al. |
| 5,842,994 A | 12/1998 | TenHoff et al. |
| 5,916,210 A | 6/1999 | Winston |
| 5,921,934 A * | 7/1999 | Teo ............................... 600/468 |
| 6,004,269 A * | 12/1999 | Crowley et al. ............... 600/439 |
| 6,036,648 A * | 3/2000 | White et al. .................. 600/459 |
| 6,101,409 A | 8/2000 | Swanson et al. |
| 6,457,365 B1 * | 10/2002 | Stephens et al. ................ 73/626 |
| 7,706,860 B2 | 4/2010 | McGee |
| 2003/0229286 A1 | 12/2003 | Lenker |
| 2007/0167813 A1 | 7/2007 | Lee et al. |
| 2009/0216125 A1 | 8/2009 | Lenker |
| 2009/0264768 A1 | 10/2009 | Courtney et al. |
| 2010/0286527 A1 | 11/2010 | Cannon et al. |

FOREIGN PATENT DOCUMENTS

| | | |
|---|---|---|
| EP | 0557127 A2 | 8/1993 |
| WO | WO2007032682 A1 | 3/2007 |

OTHER PUBLICATIONS

International Search Report and Written Opinion issued in PCT/US2012/025794, mailed Jun. 15, 2012, 10 pages.

* cited by examiner

*Primary Examiner* — Peter Luong
(74) *Attorney, Agent, or Firm* — Faegre Baker Daniels LLP

(57) ABSTRACT

Devices, systems, and methods for ultrasonically acquiring far-field and near-field images within a body are disclosed. An ultrasound imaging device adapted for insertion within a body includes a first ultrasonic sensor configured to transmit ultrasonic waves at a first frequency for acquiring far-field images within the body, and a second ultrasonic sensor configured to transmit ultrasonic waves at a higher frequency than the first frequency for acquiring near-field images within the body. The ultrasound imaging device can be connected to a control device and user interface for visualizing far-field and near-field images acquired by the ultrasonic sensors.

16 Claims, 6 Drawing Sheets

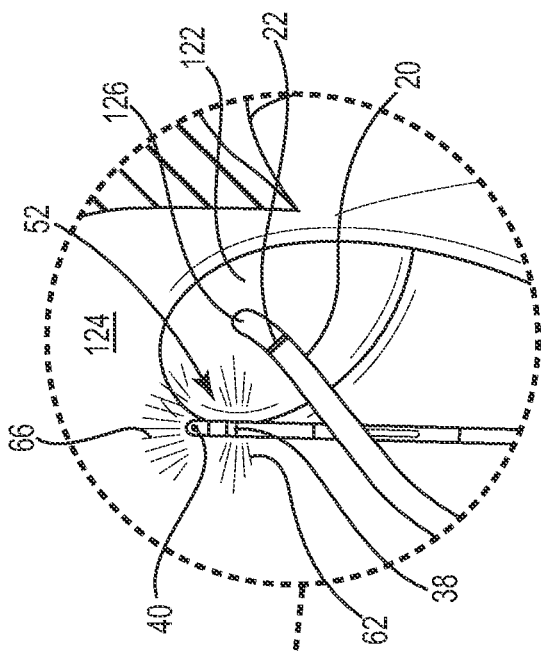
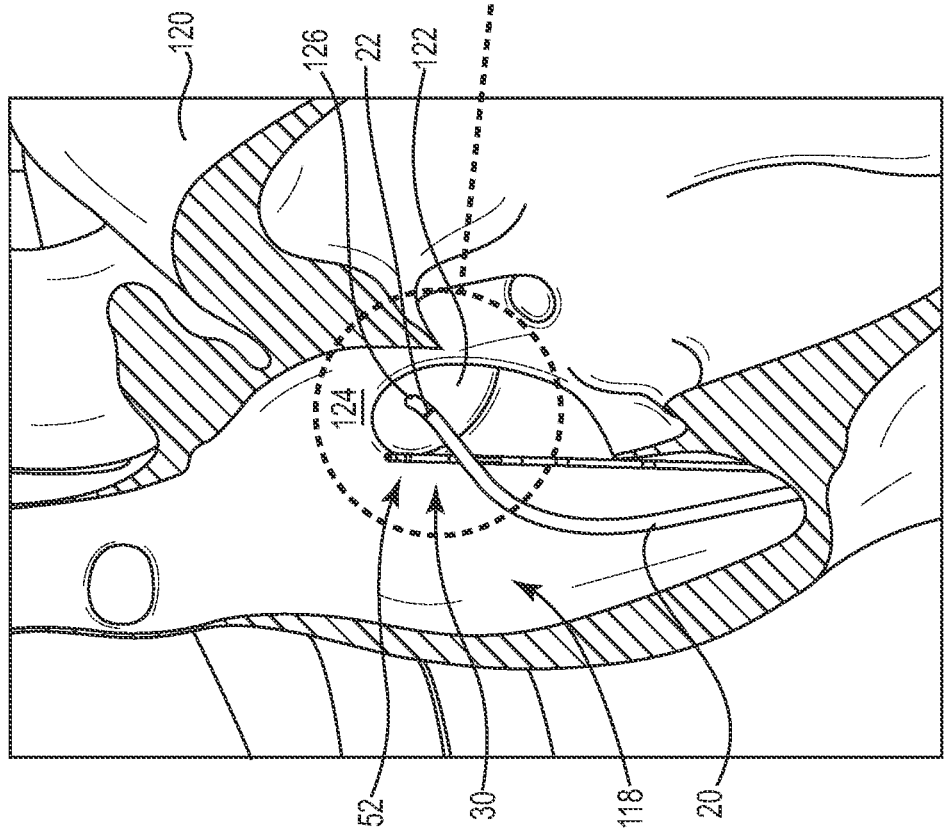

FAR-FIELD AND NEAR-FIELD ULTRASOUND IMAGING DEVICE

CROSS-REFERENCE TO RELATED APPLICATION

This application claims priority to Provisional Application No. 61/466,107, filed Mar. 22, 2011 and entitled "Far-Field and Near-Field Ultrasound Imaging Device," the contents of which are incorporated herein by reference in their entirety for all purposes.

TECHNICAL FIELD

The present disclosure relates generally to imaging devices and systems for imaging medical probes and anatomical structures within the body. More specifically, the present disclosure relates to ultrasound imaging devices and systems capable of visualizing medical probes, anatomical structures, and body tissue in both the far-field and near-field.

BACKGROUND

In many diagnosis and interventional procedures, it is often necessary to determine the location of a medical probe or catheter relative to a location of interest within the body. In interventional cardiac electrophysiology procedures, for example, it is often necessary for the physician to determine in real-time the location of a medical probe such as a electrophysiology mapping catheter or therapeutic delivering catheter (e.g., an ablation catheter) relative to the patient's internal anatomy. During such procedures, the physician may deliver the mapping catheter through a main vein or artery into an interior region of the heart to be treated. Using the mapping catheter, the physician may then determine the source of the cardiac rhythm disturbance or abnormality by placing a number of mapping elements carried by the catheter into contact with the adjacent cardiac tissue and then operating the catheter to generate an electrophysiology map of the interior region of the heart. Once a map of the heart is generated, the physician may then advance an ablation catheter into the heart, and position an ablating element carried by the catheter tip near the targeted cardiac tissue to ablate the tissue and form a lesion, thereby treating the cardiac rhythm disturbance or abnormality.

The navigation of medical probes such as mapping and ablation catheters has traditionally been accomplished using fluoroscopic techniques in which radiopaque elements located at or near the distal end of the probe are used to fluoroscopically image the probe as it is routed through the body. Such systems produce a two-dimensional image of the probe, as represented by the illuminated radiopaque element, allowing the physician to ascertain the general location of the probe. Although fluoroscopy is commonly used in EP procedures, such technique does not permit the imaging of soft tissues, making it difficult for the physician to visualize features of the anatomy as a reference for navigation.

Various ultrasound-based imaging catheters and probes have been developed for directly visualizing medical probes in applications such as interventional cardiology, interventional radiology, and electrophysiology. For interventional cardiac electrophysiology procedures, for example, ultrasound imaging devices have been developed that permit the visualization of anatomical structures of the heart directly and in real-time. In some electrophysiology procedures, for example, ultrasound catheters may be used to image the intra-atrial septum, to guide transseptal crossing of the atrial septum, to locate and image the pulmonary veins, and to monitor the atrial chambers of the heart for signs of a perforation and pericardial effusion. Many ultrasound-based imaging devices are designed to image in the far-field at a distance greater than about 1 cm, allowing the physician to visualize anatomical structures, the position of devices relative to those structures, as well as any anomalies or interesting characteristics of those structures. These devices typically operate at lower ultrasonic frequencies of between about 2 to 15 MHZ in order to balance far-field tissue/blood penetration against far-field resolution and image quality.

In some procedures, it may be desirable to visualize tissue that is in close proximity to the imaging device (e.g., at or less than about 1 cm) in order to determine the characteristics of that tissue. For example, such feedback may help the physician to determine whether the device is in contact with tissue, to determine whether the tissue is healthy tissue or scar tissue, to determine the thickness of the tissue, to determine whether an ablation lesion is transmural or continuous with adjacent lesions, as well as other characteristics.

SUMMARY

The present disclosure relates to ultrasound imaging devices and systems capable of visualizing medical probes, anatomical structures, and body tissue in both the far-field and near-field.

In Example 1, an ultrasound imaging device adapted for insertion within a body comprises an elongate housing having a proximal section and a distal section; a first ultrasonic sensor configured to operate in alternating pulsing and sensing modes, the first ultrasonic sensor disposed within the distal section and configured to transmit substantially side-directed ultrasonic waves at a first frequency for acquiring far-field images within the body; a second ultrasonic sensor disposed within a distal tip and configured to operate in alternating pulsing and sensing modes, the second ultrasonic sensor configured to transmit substantially forward-directed ultrasonic waves at a second frequency greater than the first frequency for acquiring near-field images within the body; and a means for rotating at least one of the first and second ultrasonic sensors within the housing.

In Example 2, the ultrasound imaging device of Example 1, wherein the means for rotating at least one of the first and second ultrasonic sensors includes a rotating element coupled to both the first and second ultrasonic sensors.

In Example 3, the ultrasound imaging device of Example 1, wherein the means for rotating at least one of the first and second ultrasonic sensors includes a first actuator coupled to the first ultrasonic sensor and a second actuator coupled to the second ultrasonic sensor.

In Example 4, the ultrasound imaging device of Example 1, wherein the means for rotating at least one of the first and second ultrasonic sensors includes a rotating driveshaft coupled to the first ultrasonic sensor and a motor coupled to the second ultrasonic sensor.

In Example 5, the ultrasound imaging device of any of Examples 1-4, wherein the first ultrasonic sensor is configured to direct ultrasonic waves at a transmission angle of between about 10 to 40 degrees.

In Example 6, the ultrasound imaging device of any of Examples 1-5, wherein the second ultrasound sensor is configured to direct ultrasonic waves at transmission angle of between about 10 to 40 degrees.

In Example 7, the ultrasound imaging device of any of Examples 1-6, further comprising a means for dynamically adjusting the direction of the ultrasonic waves transmitted by at least one of the first and second ultrasonic sensors.

In Example 8, the ultrasound imaging device of any of Examples 1-7, wherein the second ultrasonic sensor comprises a plurality of ultrasonic transducer elements, and wherein the means for dynamically adjusting the direction of at least one of the first and second ultrasonic waves includes a means for adjusting phase delays on one or more of the transducer elements.

In Example 9, the ultrasound imaging device of any of Examples 1-8, further comprising a steering wire configured for steering the distal section of the housing.

In Example 10, the ultrasound imaging device of any of Examples 1-9, further comprising at least one electrode configured for sensing electrical activity within the body.

In Example 11, an ultrasound imaging device adapted for insertion within a body comprises an elongate housing having a proximal section, a distal section, and a distal tip; a first ultrasonic sensor configured for acquiring far-field images within the body, the first ultrasonic sensor disposed within the distal section of the housing and configured to transmit substantially side-directed ultrasonic waves at a first frequency; and a second ultrasonic sensor configured for acquiring near-field images within the body, the second ultrasonic sensor disposed within the distal tip and configured to transmit substantially forward-directed ultrasonic waves at a second frequency greater than the first frequency.

In Example 12, an apparatus for acquiring far-field and near-field ultrasonic images within a body comprises a control device; an ultrasound imaging device coupled to the control device, the ultrasound imaging device including a housing having a proximal section and a distal section, a first ultrasonic sensor configured to transmit substantially side-directed ultrasonic waves at a first frequency for acquiring far-field images within the body, and a second ultrasonic sensor configured to transmit substantially forward-directed ultrasonic waves at a second frequency greater than the first frequency for acquiring near-field images within the body; and a user interface configured for visualizing far-field and near-field images acquired by the first and second ultrasonic sensors.

In Example 13, the apparatus of Example 12, wherein the ultrasound imaging device further includes a means for rotating at least one of the first and second ultrasonic sensors.

In Example 14, the apparatus of any of Examples 12-13, wherein the first ultrasonic sensor is disposed within the housing proximal to the second ultrasonic sensor, and is configured to transmit substantially side-directed ultrasonic waves from a side of the housing.

In Example 15, the apparatus of any of Examples 12-14, wherein the second ultrasonic sensor is disposed within a distal tip of the housing, and is configured to transmit substantially forward-directed ultrasonic waves from the housing.

In Example 16, the apparatus of any of Examples 12-15, wherein the control device includes a controller, a rotary joint, a motor encoder, and an image processor.

In Example 17, the apparatus of any of Examples 12-16, wherein the control system is configured to rotate at least one of the first and second ultrasound sensors within the housing.

In Example 18, the apparatus of any of Examples 12-17, further comprising a means for rotating the first and second ultrasonic sensors within the housing, and wherein the control device is configured for controlling the rotation of one or both of the first and second sensors.

In Example 19, the apparatus of any of Examples 12-18, further comprising a means for dynamically adjusting the direction of ultrasonic waves transmitted by at least one of the first and second ultrasonic sensors.

In Example 20, the apparatus of any of Examples 12-19, wherein at least one of the first and second ultrasonic sensors includes a plurality of transducer elements, and wherein the control device is configured to dynamically adjust the direction of ultrasonic waves transmitted by the transducer elements.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8 is a view showing an ultrasound imaging device implanted in the right atrium of the heart and configured for visualizing a medical probe relative to cardiac anatomy; and FIG. 9 is an enlarged view showing the transmission of ultrasonic waves from the ultrasound imaging device of FIG. 8.

Figure 1:
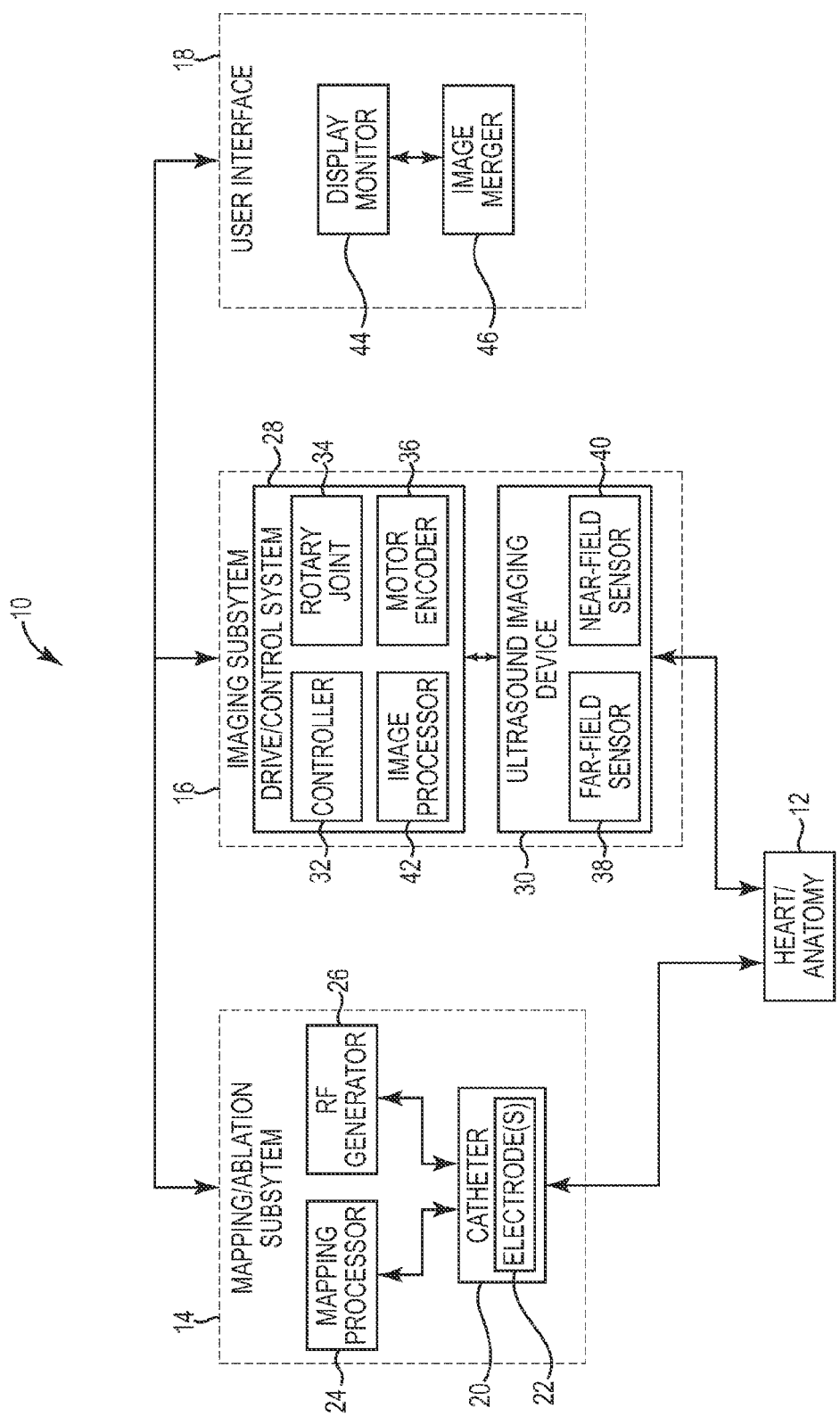
FIG. 1 is a functional block diagram showing a medical system in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a functional block diagram showing a medical system in accordance with an illustrative embodiment. The system 10, illustratively a system for mapping and treating a heart 12, includes a mapping/ablation subsystem 14 for mapping and ablating tissue within the heart 12, an imaging subsystem 16 for generating high resolution images of anatomical structures and body tissue in or near the heart 12, and a user interface 18 for registering mapping data and visualizing anatomical structures and body tissue as well as the movement of other medical devices in or near the heart 12.

The mapping/ablation subsystem 14 may be used for identifying and treating a target tissue site or multiple sites within the body such as an aberrant conductive pathway. In the embodiment of FIG. 1, the mapping/ablation subsystem 14 comprises a mapping/ablation catheter 20 including one or more sense/treatment electrodes 22, a mapping processor 24, and a radio frequency (RF) generator 26. An example mapping/ablation catheter 20 that can be operated to detect electrical signals in myocardial tissue for use in identifying target treatment sites and/or for providing ablation energy to target sites is further described, for example, in U.S. Pat. No. 7,720,520, which is expressly incorporated herein by reference in its entirety for all purposes. Other types of mapping/ablation catheters 20 can also be used. In some embodiments, for example, the catheter can comprise a basket-type structure of resilient splines each including one or more sense/ablation electrodes. In yet other embodiments, the catheter can include one or more roving sense/ablation electrodes that can be steered into contact with identified ablation sites. In some embodiments, an ablation catheter with a dedicated ablation electrode or electrodes can be used in conjunction with a separate mapping catheter.

The mapping processor 24 is configured to derive activation times and voltage distribution from the electrical signals obtained from the electrodes 22 to determine irregular electrical signals within the heart 12, which can then be graphically displayed as a map on the user interface 18. Further details regarding electrophysiology mapping are provided, for example, in U.S. Pat. Nos. 5,485,849, 5,494,042, 5,833,621, and 6,101,409, each of which are expressly incorporated herein by reference in their entirety for all purposes.

The RF generator 26 is configured to deliver ablation energy to an ablation electrode (e.g., a distal-most electrode 22 of the mapping/ablation catheter 20) in a controlled manner to ablate any sites identified by the mapping processor 24. Other types of ablation sources in addition to or in lieu of the RF generator 26 can also be used for ablating target sites. Examples of other types of ablation sources can include, but are not limited to, microwave generators, acoustic generators, cryoablation generators, and laser/optical generators. Further details regarding RF generators are provided, for example, in U.S. Pat. No. 5,383,874, which is expressly incorporated herein by reference in its entirety for all purposes.

In the embodiment of FIG. 1, the imaging subsystem 16 includes a drive and control system 28 that can be used for controlling an ultrasound imaging device 30 adapted to visualize anatomical structures, body tissue, as well as the other implanted medical devices located relative to those structures and tissue. In certain embodiments, the drive and control system 28 includes a controller 32, a rotary joint 34, and a motor encoder 36. In some embodiments, the controller 32 and rotary joint 34 are configured to control the rotation of a driveshaft 76 (see FIG. 3) that extends through an interior lumen of the ultrasound imaging device 30 to a distal section of the device 30. During this rotation, the motor encoder 36 is configured to detect the instantaneous rotational position of the driveshaft via the rotary joint 34, and provides a feedback signal containing the current driveshaft position back to the controller 32, which can then be used to generate scan images from a far-field ultrasonic sensor 38 and near-field ultrasonic sensor 40, as discussed further below. Connection of the rotary joint 34 and motor encoder 36 to the ultrasound imaging device 30 can be accomplished, for example, via a motor/drive shaft connector 58 described further herein with respect to FIG. 2.

During operation, the controller 32 is configured to monitor and control the positioning of the far-field ultrasonic sensor 38 and near-field ultrasonic sensor 40 carried by the ultrasound imaging device 30. In certain procedures, for example, the controller 32 can be configured to monitor and control the position of the ultrasound imaging device 30 within a right atrium in order to visualize the anatomy and the presence of a mapping/ablation catheter 20 within the atrium using the far-field ultrasonic sensor 38 as well as the status of soft body tissue within the atrium using the near-field ultrasonic sensor 40. As used herein, the terms "far-field" and "near-field" are relative terms that describe the ability of the ultrasonic sensors 38,40 to accurately reproduce images of anatomy and/or objects located a certain distance away from the sensor. The distance at which the sensors 38,40 can visualize anatomy and objects within the body is dependent on the mechanical characteristics of the sensors 38,40, the electrical characteristics of the sensor circuitry including the drive frequency that drives the sensors 38,40, the attenuation and boundary conditions between the sensors 38,40 and the surrounding anatomy, as well as other factors.

In some cardiac procedures such as interventional cardiac electrophysiology, the relative term "far-field" can be defined generally as a distance greater than about 1 cm away from the sensor surface whereas the relative term "near-field" can be defined generally as a distance at or less than 1 cm away from the sensor surface. The distances that define whether the sensor 38,40 generates images in the "far-field" or "near-field" can vary, however, depending on the particular procedure to be performed. In applications for detecting and treating neurological disorders, for example, the ultrasonic sensors 38,40 can each be configured to visualize objects at different relative distances than in cardiac applications due to the differing anatomy of the brain and brain tissue.

The electrical signals sensed by each of the ultrasonic sensors 38,40 can be fed to an imaging processor 42, which combines the signals with the positioning information from the controller 32 to produce both a far-field image and a near-field image on a display monitor 44 of the user interface 18. In some embodiments, an image merger 46 is configured to superimpose graphical information from the medical image data acquired from the imaging subsystem 16 and superimpose that information on the display monitor 44 along with graphical information acquired from other sources (e.g., a fluoroscopic monitor) and/or position information from the mapping/ablation subsystem 14 to form a composite medical image.

Although the system 10 is described in the context of a mapping and ablation system for use in intracardiac electrophysiology procedures for diagnosing and treating the heart, in other embodiments the system 10 may be used for treating, diagnosing, or otherwise visualizing other anatomical bodies such as the prostate, brain, gall bladder, uterus, esophagus, and/or other regions in the body. Moreover, many of the elements in FIG. 1 are functional in nature, and are not meant to limit the structure that performs these functions in any manner. For example, several of the functional blocks can be embodied in a single device, or one or more of the functional blocks can be embodied in multiple devices.

Figure 2:
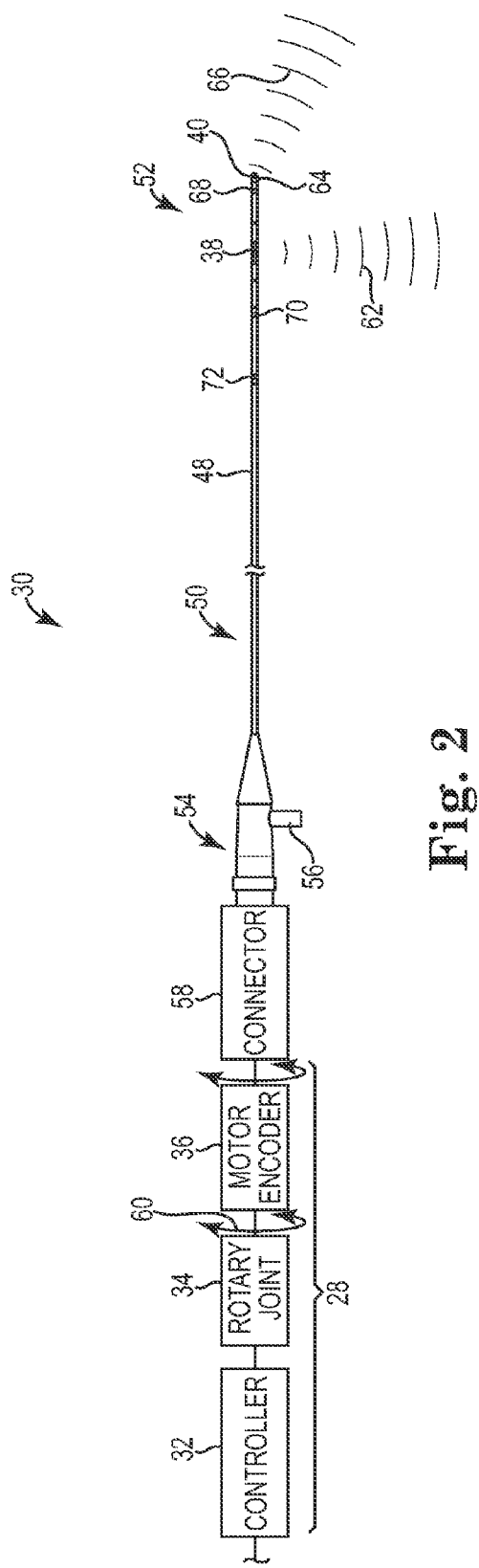
FIG. 2 is a schematic view showing an ultrasound imaging device in accordance with an illustrative embodiment.

FIG. 2 is a schematic view showing an ultrasound imaging device 30 in accordance with an illustrative embodiment for use with the system 10 of FIG. 1. As shown in FIG. 2, the ultrasound imaging device 30 includes an elongate tubular housing 48 having a proximal section 50 and a distal section 52. The proximal section 50 of the housing 48 is coupled to a proximal hub 54, which includes a fluid port 56 for providing acoustic coupling/cooling fluid to one or both of the ultrasonic sensors 38,40. The proximal hub 54 is connected to the drive and control system 28 via a connector 58, which supports the hub 54 in a stationary position as the rotary joint 34 applies rotary motion 60 to rotate each of the ultrasonic sensors 38,40 within the housing 48.

In some embodiments, the ultrasonic sensors 38,40 each comprise piezoelectric transducers formed of a polymer such as PVDF or a piezoceramic material such as PZT. A number of leads (not shown) that extend through the interior space of the housing 48 connect the ultrasonic sensors 38,40 to the drive and control system 28. During ultrasonic imagining, each of the ultrasonic sensors 38,40 are configured to operate in alternating pulsing and sensing modes. When excited electrically in the pulsing mode, the ultrasonic sensor 38,40 creates pressure waves 62,66 which travel through the housing 48 and into the surrounding environment. In the sensing mode, the ultrasonic sensors 38,40 each produce an electrical signal as a result of receiving acoustic waves reflected back to the sensors 38,40, which are then processed and displayed on the display monitor 44 of the user interface 18. These reflections are generated by the acoustic waves 62,66 traveling through changes in density in the surrounding environment being imaged.

In the embodiment of FIG. 2, the far-field ultrasonic sensor 38 is located at a position along the housing 48 proximal to the near-field ultrasonic sensor 40, and is configured to transmit and receive acoustic waves 62 from the side of the housing 48 for visualizing anatomical structures and/or other medical devices in the far-field. In certain embodiments, for example, the far-field ultrasonic sensor 38 is configured to deliver acoustic waves 62 at a frequency of between about 2 to 15 MHz and in a side-oriented direction that is substantially perpendicular to a length of the housing 48. The near-field ultrasonic sensor 40, in turn, is located at or near the distal tip 64 of the housing 48, and is configured to transmit and receive acoustic waves 66 in a substantially forward-oriented direction for visualizing body tissue and other structures in the near-field. In certain embodiments, for example, the near-field ultrasonic sensor 40 is configured to deliver acoustic waves 66 at a frequency greater than about 20 MHz and in a forward-oriented direction from the distal tip 64 of the housing 48.

The ultrasound imaging device 30 further includes a radiopaque marker 68 that can be used to fluoroscopically monitor the location of the device 30 within the body. In some embodiments, the device 30 also includes one or more electrodes 70,72 on its outer surface to permit the recording of electrical signals, and in some cases, the delivery of electrical signals. In certain embodiments, the electrodes 70,72 can also be used to facilitate position tracking of the device 30 using a position tracking system. Although the device 30 shown in FIG. 2 includes a single far-field ultrasonic sensor 38 and a single near-field ultrasonic sensor 40, in other embodiments multi far-field and/or near-field ultrasonic sensors can be employed. Moreover, the location of each of the sensors 38,40 can vary. In some embodiments, for example, the far-field ultrasonic sensor 38 is configured to transmit acoustic waves 62 primarily in a forward direction from the distal tip 64 whereas the near-field ultrasonic sensor 40 is configured to transmit side-oriented acoustic waves 66 from the side of the housing 48. Other configurations are also possible.

Figure 3:
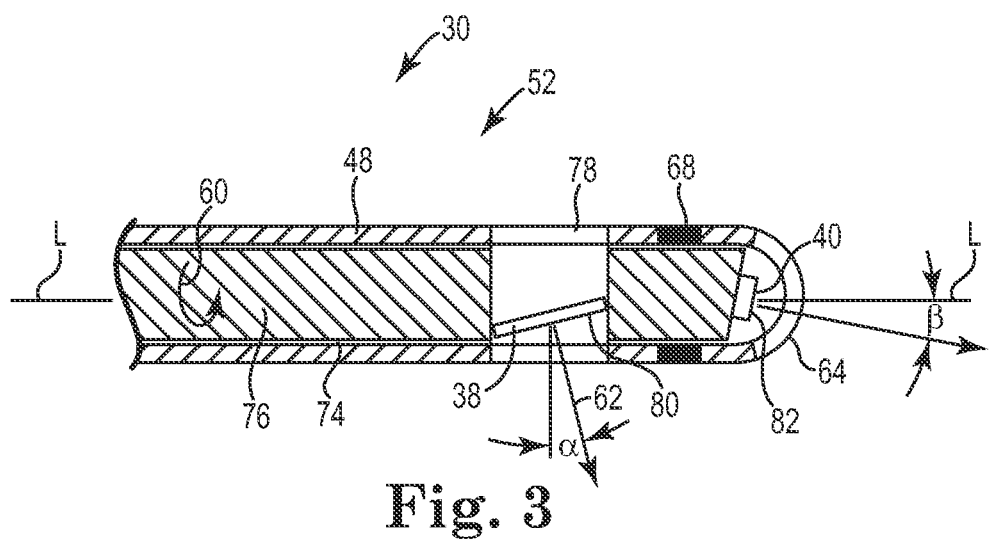
FIG. 3 is a schematic view showing the distal section of the ultrasound imaging device of FIG. 2 in greater detail.

FIG. 3 is a schematic view showing the distal section 52 of the ultrasound imaging device 30 of FIG. 2 in greater detail. As can be further seen in FIG. 3, and in some embodiments, an interior space 74 within the housing 48 houses a rotating driveshaft 76 coupled to each of the ultrasonic sensors 38,40. The driveshaft 76 serves as mechanical link from the drive and control system 28 to the ultrasonic sensors 38,40. In some embodiments, the rotating driveshaft 76 may further serve as an electrical link for one or both of the ultrasonic sensors 38,40 for conveying electrical signals back and forth between the sensors 38,40 and signal processing circuitry of the controller 32.

During imaging, rotary motion 60 from the driveshaft 76 vis-à-vis the drive and control system 28 is used to rotate each of the ultrasonic sensors 38,40 within the interior space 74. This rotary motion imparted to the ultrasonic sensors 38,40 serves to sweep the acoustic waves 62,66 within the anatomical space surrounding the device 30, providing the operator with a larger field of view and, in some cases, allowing the operator to view adjacent objects without having to reposition the device 30 within the body. Rotary motion from the driveshaft 76 to the far-field ultrasonic sensor 38, for example, causes the sensor 38 to direct the acoustic waves 62 360° in a field of view perpendicular to a longitudinal axis of the housing 48, allowing the operator to view anatomical structures and other medical devices in the far-field. Rotary motion from the driveshaft 76 to the near-field ultrasonic sensor 40, in turn, causes the sensor 40 to direct the acoustic waves 62 in a conical-shaped field of view in front of the device 30, allowing the operator to determine various tissue characteristics of adjacent body tissue in the near-field.

An acoustically transparent window or aperture 78 within the wall of the housing 48 facilitates the transmission of acoustic waves 62 from the far-field ultrasonic sensor 38 through the housing 48 and into the surrounding anatomy. The distal tip 64 further serves as an acoustic window or aperture to facilitate the transmission of acoustic waves 66 from the near-field ultrasonic sensor 38 through the tip 64 and into the surrounding anatomy. In some embodiments, an acoustic coupling fluid within the interior space 74 of the housing 48 serves to couple the acoustic energy transmitted and received via the ultrasonic sensors 38,40 to the anatomy surrounding the device 30. In some cases, the fluid 56 located within the interior space 74 of the housing 48 may also serve to cool the ultrasonic sensors 38,40 during use.

In some embodiments, the face 80 of the far-field ultrasonic sensor 38 is oriented in a slightly forward direction at a transmission angle $\alpha$ relative to a transverse line that is perpendicular to the longitudinal axis L of the housing 48. In certain embodiments, for example, the sensor face 80 can be oriented at a transmission angle $\alpha$ of between about 0 to 60 degrees, and more specifically about 10 to 40 degrees off-axis. During imaging, the orientation of the sensor face 80 directs the acoustic wave 62 in a slight forward direction, allowing the operator to better view anatomy and objects that are located distally of the ultrasonic sensor 38. As further shown in FIG. 3, and in some embodiments, the face 82 of the near-field ultrasonic sensor 40 is also oriented at a transmission angle $\beta$ relative to the longitudinal axis of the housing 48. In certain embodiments, for example, the sensor face 82 can be oriented at a transmission angle $\beta$ of between about 0 to 60 degrees, and more specifically, about 10 to 40 degrees off-axis. During imaging, this orientation of the sensor face 82 serves to increase the effective field of view of the near-field ultrasonic sensor 40.

In the embodiment of FIG. 3, the angles $\alpha$, $\beta$ at which each of the sensors 38,40 are oriented within the housing 48 are fixed. In other embodiments, however, the transmission angles $\alpha$, $\beta$ of the sensors 38,40 can be made adjustable to permit the operator to alter the direction of the acoustic waves 62,66 relative to the device 30. In certain embodiments, for example, one or both of the ultrasonic sensors 38,40 can be coupled to an independent servo motor that can be used to independently adjust the angle of the sensor faces 80,82 during imaging.

The ultrasonic sensors 38,40 can comprise a single ultrasonic element or multiple transducer elements. In those embodiments which employ multiple transducer elements, beam steering techniques may be used to alter the direction of the acoustic waves 62,66 at specific angles relative to the device 30. In certain embodiments, for example, phase delays may be provided on all or a subset of the transducer elements to focus the acoustic waves 62,66 towards a target imaging location, allowing the operator to direct the acoustic energy on a desired anatomical structure, tissue sample, or other location within body for further analysis. Other means for altering the direction, size, shape, as well as other characteristics of the acoustic waves 62,66 can also be employed. In some embodiments, for example, an acoustic lens may be used to focus the acoustic energy towards a particular location within the body.

Figure 4:
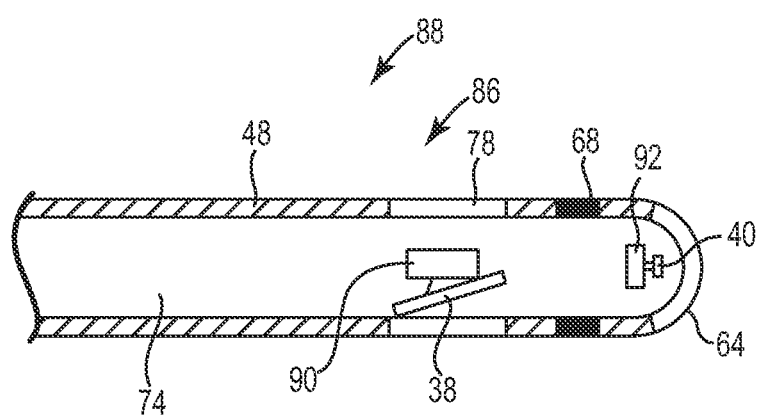
FIG. 4 is a schematic view showing the distal section of an ultrasound imaging device in accordance with another illustrative embodiment.

FIG. 4 is a schematic view showing the distal section 86 of an ultrasound imaging device 88 in accordance with another illustrative embodiment. The device 88 is similar to the device 30 shown in FIG. 3, with like elements labeled in like fashion in the figures. In the embodiment of FIG. 4, however, each of the ultrasonic sensors 38, 40 are coupled to a respective actuator 90,92 that rotates each of sensors 38,40 within the interior space 74 of the housing 48. A first motor 90 coupled to the far-field ultrasonic sensor 38, for example, is configured to independently rotate the ultrasonic sensor 38 360° in a field of view perpendicular to the longitudinal axis of the housing 48, allowing the operator to view anatomical structures and other medical devices adjacent to the device 30. A second motor 92, in turn, is coupled to the near-field ultrasonic sensor 40, and is configured to rotate the near-field ultrasonic sensor 40 within the distal tip 64 to view body tissue and other anatomy/objects in a forward-oriented direction.

Although the device 88 in FIG. 4 utilizes multiple, discrete actuators 90,92 to independently rotate each of the ultrasonic sensors 38,40, in other embodiments a single actuator (e.g., a motor) may be used to rotate each of the ultrasonic sensors 38,40 simultaneously. Moreover, additional actuators may be employed to permit the independent adjustment of the transmission angle of each of the ultrasonic sensors 38,40 in addition to the actuators 90,92 used for rotating the sensors 38,40 within the housing 48.

Figure 5:
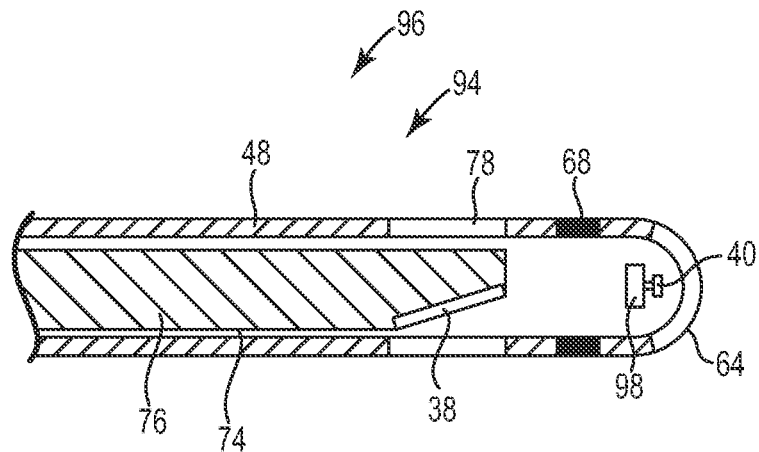
FIG. 5 is a schematic view showing the distal section of an ultrasound imaging device in accordance with another illustrative embodiment.

FIG. 5 is a schematic view showing the distal section 94 of an ultrasound imaging device 96 in accordance with another illustrative embodiment. The device 96 is similar to the device 30 shown in FIG. 3, with like elements labeled in like fashion in the figures. In the embodiment of FIG. 5, however, the driveshaft 76 is coupled to only the far-field ultrasonic sensor 38 and a separate actuator 98 is used to independently rotate the near-field ultrasonic sensor 40. As with other embodiments herein, additional actuators may be employed to adjust the transmission angle of each of the ultrasonic sensors 38,40.

Figure 6:
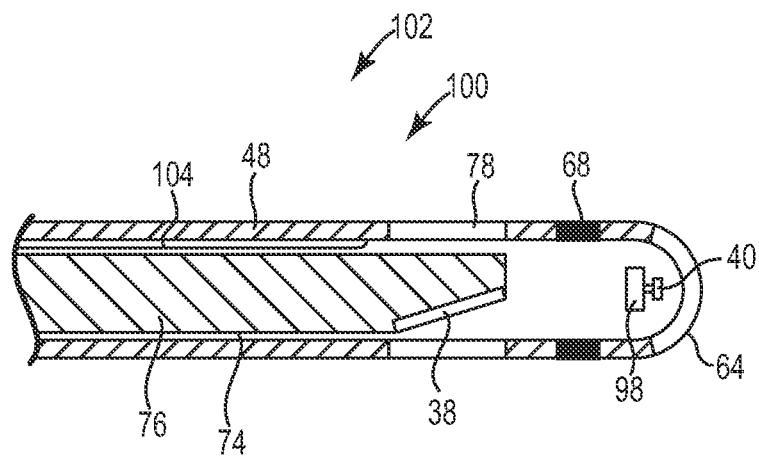
FIG. 6 is a schematic view showing the distal section of an ultrasound imaging device in accordance with another illustrative embodiment.

FIG. 6 is a schematic view showing the distal section 100 of an ultrasound imaging device 102 in accordance with another illustrative embodiment. The device 102 is similar to the device 30 shown in FIG. 3, with like elements labeled in like fashion in the figures. In the embodiment of FIG. 6, the device 102 further includes a steering wire 104 that can be used to used to steer the distal tip 64 within the body, allowing the operator to further direct the acoustic energy towards a particular location within the body. A similar steering wire can also be employed in other embodiments described herein in order to permit the operator to steer the distal tip within the body.

Figure 7:
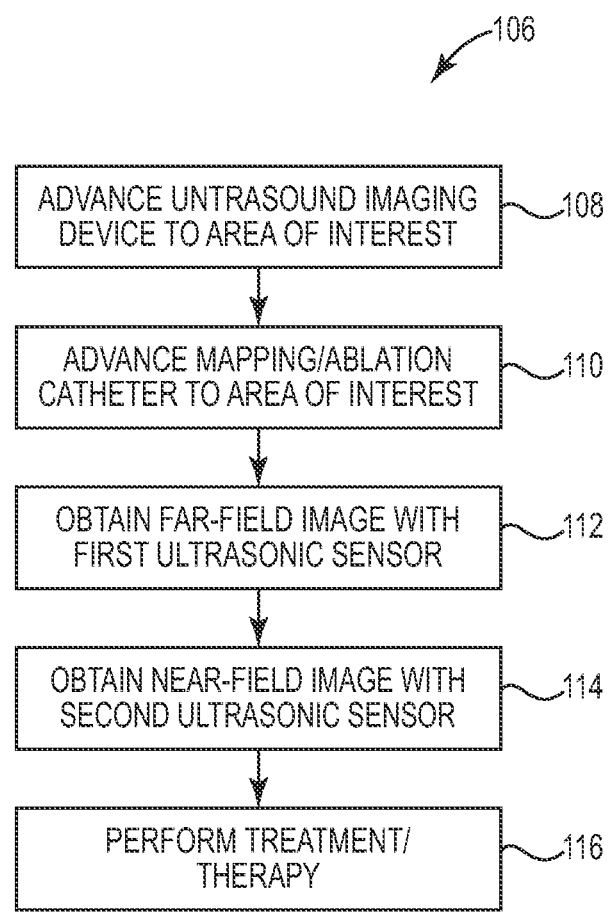
FIG. 7 is a flow diagram showing an illustrative process for visualizing anatomical structures, body tissue, and other medical devices within the body using the ultrasound imaging device of FIG. 2.

FIG. 7 is a flow diagram showing an illustrative process 106 for visualizing anatomical structures, body tissue, and other medical devices within the body using the ultrasound imaging device 30 of FIG. 2. FIG. 7 may represent, for example, several steps that can be used during a mapping and ablation procedure to visualize a mapping/ablation catheter and the surrounding anatomy during an interventional cardiac electrophysiology procedure.

The process 106 may begin generally at block 108, in which the ultrasound imaging device 30 is inserted into the body and advanced intravascularly to an area of interest within the body. In certain electrophysiology procedures, for example, the device 30 may be inserted into the body via an artery or vein (e.g., the femoral artery) and advanced through the body under fluoroscopic guidance to an area of interest such as the fossa ovalis of the right atrium. One or more additional devices may also be inserted into the body and advanced to the area of interest (block 110). In a mapping and ablation electrophysiology procedure, for example, a mapping/ablation catheter may be inserted into the body and advanced to a location within the body under fluoroscopic guidance for identifying and treating target ablation sites in or near the heart.

With the ultrasound imaging device 30 positioned at the area of interest, the operator may then activate one or both of the ultrasonic sensors 38,40 to visualize anatomical structures at the area of interest as well as the positioning of any other device(s) relative to those structures. The ultrasonic sensors 38,40 can be activated to produce images of the environment surrounding the device 30, either simultaneously or at different times during the procedure. In some embodiments, for example, the far-field ultrasonic sensor 38 may be activated to gather general information about the anatomy at the area of interest, and to determine the precise position of any other device or devices located within the body using a tracking subsystem (block 112). Based on images obtained from the far-field sensor 38, the operator may then select one or more further sites at the area for further analysis using the near-field ultrasonic sensor 40 (block 114). If, for example, the operator detects a potential target ablation site within the heart using a mapping/ablation catheter, the operator may advance the ultrasound imaging device 30 to the target area to determine whether the tissue is healthy tissue, to determine whether an ablation lesion is transmural or continuous with adjacent lesions, or to determine other characteristics of the tissue. In some procedures, the images produced by the near-field ultrasonic sensor 40 can be used to confirm whether the mapping/catheter is in contact with the tissue to be treated. In some embodiments, the images received from each of the ultrasonic sensors can be combined together with other images to obtain a composite image. For example, the ultrasonic images can be combined with images from a fluoroscope, CT-scan, MRI-scan, and/or other source to obtain a composite image.

Based on the images generated by the ultrasound imaging device 30, the operator may then perform the treatment on the patient. If, for example, an aberrant conductive pathway in the heart is identified using a mapping/ablation catheter, the operator may then position the catheter at the site of the pathway under direct visualization with one or both of the ultrasonic sensors 38,40 and perform ablation therapy on the pathway to treat the heart (block 116).

FIG. 8 is a view showing the ultrasound imaging device 30 of FIG. 2 implanted in the right atrium 118 of the heart 120 and configured for visualizing a medical probe 20 relative to surrounding cardiac anatomy. In the example procedure shown in FIG. 8, the ultrasound imaging device 30 is shown inserted into the right atrium 118 (e.g., via the inferior vena cava or abdominal aorta) and positioned at an area of interest near the fossa ovalis 122. A medical probe such as a mapping/ablation catheter 20 is also shown inserted into the body and advanced to the area of interest. The ultrasound imaging device 30 and mapping/ablation catheter 20 can be positioned in the body, for example, by percutaneous introduction through an introducer sheath inserted via an artery or vein (e.g., via a femoral artery and inferior vena cava) using fluoroscopy.

Once both devices 20,30 are positioned at the area of interest, and as can be further seen in an enlarged view in FIG. 9, the far-field and near-field ultrasonic sensors 38, 40 can be activated to generate acoustic waves 62, 66 within the surrounding anatomy. The ultrasonic sensors 38, 40 can be activated either simultaneously or at different times, depending on the procedure. In the example procedure shown in FIG. 9, for example, both the far-field and near-field ultrasonic sensors are activated simultaneously, allowing the operator to simultaneously visualize the mapping/ablation catheter 20 and fossa ovalis 122 in the far-field using the far-field ultrasonic sensor 38, and cardiac tissue 124 located at the site of the fossa ovalis 122 in the near-field using the near-field ultrasonic sensor 40. In other embodiments, the process of visualizing anatomical structures and objects in the far-field and body tissue in the near-field can be performed at different times during the procedure.

If, during the procedure, the operator desires to further visualize anatomy or objects within the body, the operator may readjust the position of the ultrasonic imaging device 30 within the body. In certain embodiments, for example, the positioning can be changed by advancing or retracting the ultrasonic imaging device 30, and/or by manipulating a steering wire coupled to the distal section 52. In some embodiments, an actuator coupled to the ultrasonic sensor 38, 40 and/or beamsteering techniques can also be used to adjust the transmission angle of the acoustic waves 62, 66 transmitted by each of the ultrasound sensors 38, 40.

As the mapping/ablation catheter 20 is moved around within the heart under direct visualization from the ultrasound imaging device 30, the mapping processor is operated to record electrical activity within the heart and derive mapping data. If an aberrant region is identified, the distal tip 126 of the catheter 20 is placed into contact with the targeted ablation region. In some procedures, the near-field ultrasonic sensor 40 can be advanced to a location adjacent to the site of the catheter distal tip 126 to ensure that the tip 126 is engaged against the target tissue at the precise location identified via the mapping data. An RF generator is then operated to begin ablating the tissue, and if instability in the catheter 20 is detected, additional images of the catheter 20 and tissue adjacent to the catheter can be taken to ensure that the catheter 20 is still properly positioned. If necessary, the operator may then readjust the positioning of the catheter 20 until the ablation is complete. The process can then be performed for any additional target tissue sites that are identified.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An ultrasound imaging device adapted for insertion within a body, comprising:
    an elongate housing having a longitudinal axis, a proximal section, a distal section, a first acoustic window extending circumferentially about the housing, a second acoustic window defining a distal tip of the housing, and an interior space within the housing extending from the proximal section to the distal section, the proximal section connected to a proximal hub that is proximal of the proximal section;
    a first ultrasonic sensor configured to operate in alternating pulsing and sensing modes, the first ultrasonic sensor disposed within the distal section of the housing and configured to transmit substantially side-directed ultrasonic waves through the first acoustic window at a first frequency for acquiring far-field images within the body;
    second ultrasonic sensor disposed on the longitudinal axis configured to operate in alternating pulsing and sensing modes, the second ultrasonic sensor disposed within a distal tip of the housing and configured to transmit substantially forward-directed ultrasonic waves through the second acoustic window at a second frequency greater than the first frequency for acquiring near-field images within the body;
    a drive motor proximal of the proximal hub; and
    a drive shaft extending through the proximal hub and further extending within the interior space of the housing from the proximal section to the distal section, the drive shaft rotatable by the drive motor, each of the first and ultrasonic sensors connected to the drive shaft such that the first and second ultrasonic sensors rotate with the drive shaft relative to the housing and the first and second acoustic windows.

2. The ultrasound imaging device of claim 1, wherein the first ultrasonic sensor is configured to direct ultrasonic waves at a transmission angle of between about 10 to 40 degrees relative to a transverse line that is perpendicular to a longitudinal axis of the elongate housing.

3. The ultrasound imaging device of claim 1, wherein the second ultrasound sensor is configured to direct ultrasonic waves at a transmission angle of between about 10 to 40 degrees relative to a longitudinal axis of the elongate housing.

4. The ultrasound imaging device of claim 1, further comprising a means for dynamically adjusting the direction of the ultrasonic waves transmitted by at least one of the first and second ultrasonic sensors.

5. The ultrasound imaging device of claim 4, wherein the second ultrasonic sensor comprises a plurality of ultrasonic transducer elements, and wherein the means for dynamically adjusting the direction of at least one of the first and second ultrasonic waves includes a means for adjusting phase delays on one or more of the transducer elements.

6. The ultrasound imaging device of claim 1, further comprising a steering wire configured for steering the distal section of the housing.

7. The ultrasound imaging device of claim 1, further comprising at least one electrode configured for sensing electrical activity within the body.

8. An ultrasound imaging device adapted for insertion within a body, comprising:
    an elongate housing having a longitudinal axis, a proximal section, a distal section, and a distal tip;
    a proximal hub connected to the proximal section and proximal of the proximal section;

a first ultrasonic sensor configured for acquiring far-field images within the body, the first ultrasonic sensor disposed within the distal section of the housing and configured to transmit substantially side-directed ultrasonic waves at a first frequency;

a second ultrasonic sensor disposed on the longitudinal axis configured for acquiring near-field images within the body, the second ultrasonic sensor disposed within the distal tip and configured to transmit substantially forward-directed ultrasonic waves at a second frequency greater than the first frequency; and a drive shaft that extends within the proximal hub, the proximal section, the distal section, and the distal tip, the first and the second ultrasonic sensors connected to the drive shaft and rotatable relative to the elongate housing by the drive shaft.

9. An apparatus for acquiring far-field and near-field ultrasonic images within a body, comprising:

a control device;

an ultrasound imaging device coupled to the control device, the ultrasound imaging device including a housing having a longitudinal axis, a proximal section and a distal section, a first ultrasonic sensor having a face orientated and configured to transmit substantially side-directed ultrasonic waves at a first frequency for acquiring far-field images within the body, the face of the first ultrasonic sensor oriented in a slightly forward direction to transmit the substantially side-directed ultrasonic waves in a slight forward direction, and a second ultrasonic sensor disposed on the longitudinal axis having a face orientated and configured to transmit substantially forward-directed ultrasonic waves at a second frequency greater than the first frequency for acquiring near-field images within the body, the face of the second ultrasonic sensor oriented in a slightly sideways direction to transmit the substantially forward-directed ultrasonic waves in a slight sideways direction, wherein the control device is configured to rotate at least one of the first and second ultrasound sensors relative to the housing; and a user interface configured for visualizing far-field and near-field images acquired by the first and second ultrasonic sensors.

10. The apparatus of claim 9, wherein the ultrasound imaging device further includes a means for rotating at least one of the first and second ultrasonic sensors.

11. The apparatus of claim 9, wherein the first ultrasonic sensor is disposed within the housing proximal to the second ultrasonic sensor, and is configured to transmit substantially side-directed ultrasonic waves from a side of the housing.

12. The apparatus of claim 9, wherein the second ultrasonic sensor is disposed within a distal tip of the housing, and is configured to transmit substantially forward-directed ultrasonic waves from the housing.

13. The apparatus of claim 9, wherein the control device includes a controller, a rotary joint, a motor encoder, and an image processor.

14. The apparatus of claim 9, further comprising a means for rotating the first and second ultrasonic sensors within the housing, and wherein the control device is configured for controlling the rotation of one or both of the first and second sensors.

15. The apparatus of claim 9, further comprising a means for dynamically adjusting the direction of ultrasonic waves transmitted by at least one of the first and second ultrasonic sensors.

16. The apparatus of claim 9, wherein at least one of the first and second ultrasonic sensors includes a plurality of transducer elements, and wherein the control device is configured to dynamically adjust the direction of ultrasonic waves transmitted by the transducer elements.

* * * * *